US011992655B2

United States Patent
Adams et al.

(10) Patent No.: US 11,992,655 B2
(45) Date of Patent: May 28, 2024

(54) SYSTEMS AND METHODS FOR IMPROVING OPERATION OF INFUSION PUMPS

(71) Applicant: Smiths Medical ASD, Inc., Plymouth, MN (US)

(72) Inventors: Grant Adams, Anoka, MN (US); James Drost, Woodbury, MN (US); Ryan Heilman, Andover, MN (US)

(73) Assignee: Smiths Medical ASD, Inc., Plymouth, MN (US)

( * ) Notice: Subject to any disclaimer, the term of this patent is extended or adjusted under 35 U.S.C. 154(b) by 659 days.

(21) Appl. No.: 17/250,093

(22) PCT Filed: May 28, 2019

(86) PCT No.: PCT/US2019/034180
§ 371 (c)(1),
(2) Date: Nov. 24, 2020

(87) PCT Pub. No.: WO2019/227098
PCT Pub. Date: Nov. 28, 2019

(65) Prior Publication Data
US 2021/0308375 A1 Oct. 7, 2021

Related U.S. Application Data

(60) Provisional application No. 62/676,590, filed on May 25, 2018.

(51) Int. Cl.
*A61M 5/168* (2006.01)
*A61M 5/142* (2006.01)

(52) U.S. Cl.
CPC ........ *A61M 5/16831* (2013.01); *A61M 5/142* (2013.01); *A61M 5/16804* (2013.01);
(Continued)

(58) Field of Classification Search
CPC .............. A61M 5/16831; A61M 5/142; A61M 5/16804; A61M 5/16886; A61M 5/168;
(Continued)

(56) References Cited

U.S. PATENT DOCUMENTS 4,828,545 A * 5/1989 Epstein ............. A61M 5/14224
604/67
5,153,827 A 10/1992 Coutre et al.
(Continued)

FOREIGN PATENT DOCUMENTS

CN 112188905 A 1/2021
EP 1529546 B1 5/2005
(Continued)

OTHER PUBLICATIONS

International Search Report and Written Opinion from PCT Application PCT/US2019/034180, dated Sep. 11, 2019, 12 pgs.

*Primary Examiner* — Tasnim Mehjabin Ahmed
(74) *Attorney, Agent, or Firm* — Husch Blackwell

(57) ABSTRACT

Infusion pumps and associated methods for delivering medicament to a user during error conditions. An infusion pump can include a sensor, a pumping mechanism to deliver medicament through an infusion set to the user, and a processor operably coupled to the sensor and the pumping mechanism. The processor can be configured to receive an indication from the sensor of an error condition, and continue operating the pumping mechanism to deliver a predetermined quantity of medicament without correcting the error condition. The predetermined quantity can be based at least in part on a characteristic of the infusion set.

11 Claims, 4 Drawing Sheets

(52) U.S. Cl.
CPC ..... *A61M 5/16886* (2013.01); *A61M 2205/18* (2013.01); *A61M 2205/50* (2013.01)

(58) Field of Classification Search
CPC .......... A61M 2205/18; A61M 2205/50; A61M 2005/14208; A61M 2005/16863
See application file for complete search history.

(56) References Cited

U.S. PATENT DOCUMENTS

| | | | |
|---|---|---|---|
| 5,630,710 A | | 5/1997 | Tune et al. |
| 5,643,212 A | * | 7/1997 | Coutre ................... G16H 20/17 |
| | | | 128/DIG. 13 |
| 8,182,461 B2 | | 5/2012 | Pope et al. |
| 8,900,213 B2 | | 12/2014 | Pope et al. |
| 9,427,521 B2 | | 8/2016 | Pope et al. |
| 2006/0140798 A1 | | 6/2006 | Kutsuzawa |
| 2006/0184154 A1 | | 8/2006 | Moberg et al. |
| 2010/0185142 A1 | | 7/2010 | Kamen et al. |
| 2010/0262078 A1 | | 10/2010 | Blomquist |
| 2011/0040247 A1 | * | 2/2011 | Mandro .............. A61M 5/5086 |
| | | | 604/67 |
| 2012/0293328 A1 | | 11/2012 | Blomquist |
| 2013/0245599 A1 | | 9/2013 | Williams et al. |
| 2014/0039446 A1 | | 2/2014 | Day |
| 2014/0100526 A1 | | 4/2014 | Ueda et al. |
| 2014/0122739 A1 | | 5/2014 | Thang et al. |
| 2015/0359966 A1 | | 12/2015 | Day et al. |
| 2017/0095638 A1 | | 4/2017 | Young et al. |
| 2017/0203036 A1 | | 7/2017 | Mazlish et al. |

FOREIGN PATENT DOCUMENTS

| | | |
|---|---|---|
| EP | 1616589 B1 | 1/2006 |
| EP | 1930039 B1 | 6/2008 |
| EP | 3290071 A1 | 3/2018 |
| JP | 2012-205929 | 10/2012 |
| JP | 2017-517365 | 6/2017 |
| JP | 2017-136435 | 8/2017 |
| JP | 2021525554 A | 9/2021 |
| WO | WO 2009/146080 A2 | 12/2009 |
| WO | 2011131790 A1 | 10/2011 |
| WO | 2014/122739 A1 | 8/2014 |
| WO | WO 2019/227098 A1 | 11/2019 |

* cited by examiner

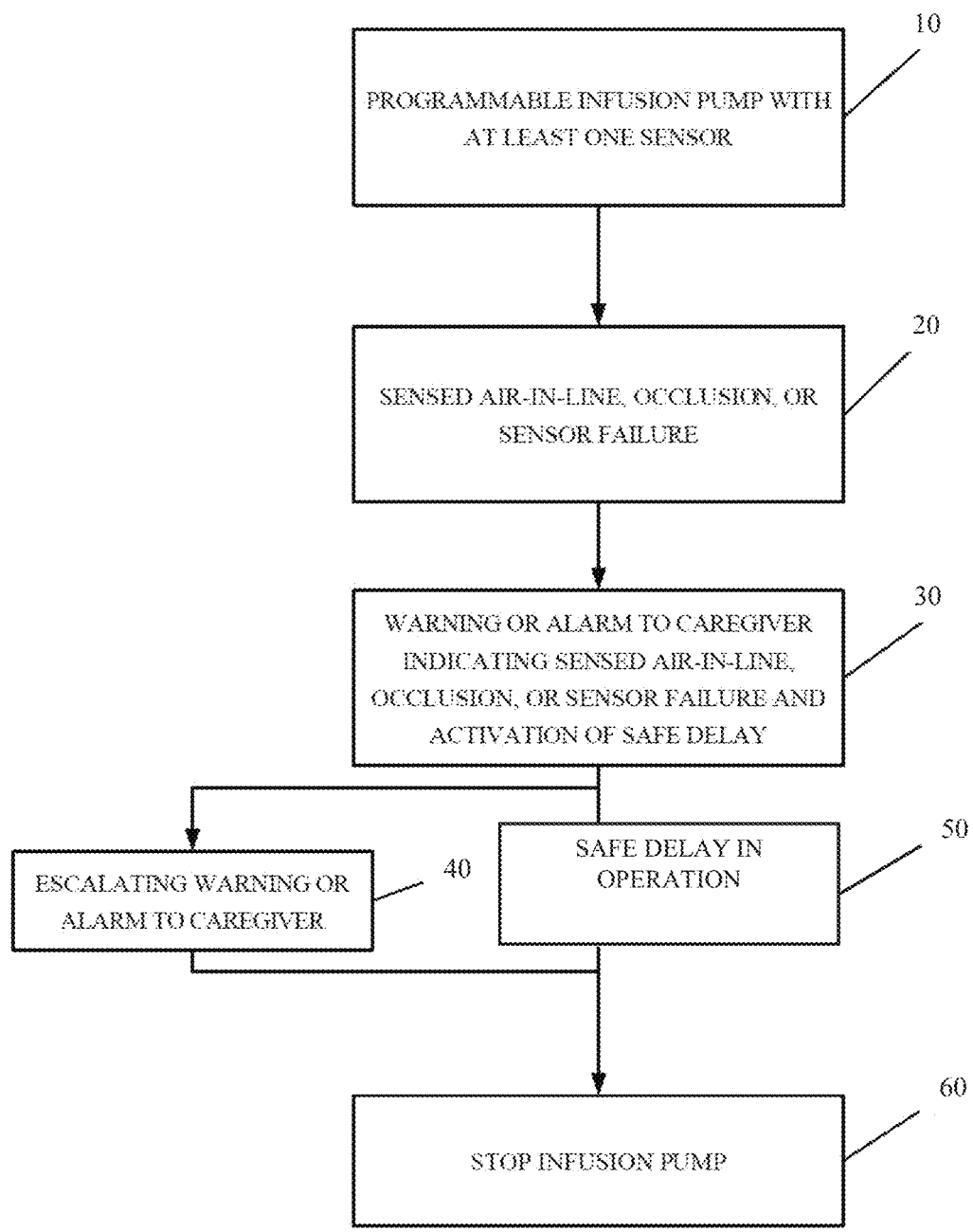

SYSTEMS AND METHODS FOR IMPROVING OPERATION OF INFUSION PUMPS

CROSS-REFERENCE TO RELATED APPLICATION

The present application is a National Phase entry of PCT Application No. PCT/US2019/034180, filed May 28, 2019, which claims the benefit of U.S. Provisional Application No. 62/676,590 filed May 25, 2018, the disclosures of which are hereby incorporated by reference in their entireties.

TECHNICAL FIELD

The subject matter hereof relates generally to medical devices, and more particularly, to systems and methods for improving the operation of infusion pumps.

BACKGROUND

Infusion pumps are useful medical devices for providing prescribed fluids, drugs, and other therapies to patients. For example, medications (alternately, infusates or medicaments) such as antibiotics, chemotherapy drugs, anesthetics, and pain relievers are commonly delivered to patients via infusion pumps, as are nutrients and other supplements. Infusion pumps are used in hospitals, nursing homes, and in other short-term and long-term medical facilities, as well as for in-home care. Infusion pumps can be particularly useful for the delivery of medical therapies requiring an extended period of time for administration of medicament. Types of infusion pumps include large volume (LVP), patient-controlled analgesia (PCA), elastomeric, syringe, enteral, and insulin pumps. Infusion pumps are typically useful in various routes of medication delivery, including intravenously, intra-arterially, intradermally, subcutaneously, intraperitoneally, in close proximity to nerves, and into an intraoperative site, epidural space or subarachnoid space.

Operation of an infusion pump is typically controlled by a configuration of computerized or microprocessor-based software. This control configuration can reside locally within the pump by way of suitable hardware and software or remotely via a suitable communication path, wired or wireless, by way of suitable hardware and software outside of the pump such as in a network computer. A practitioner such as a properly trained physician or a nurse can therefore configure an infusion pump to operate according to a delivery profile that corresponds to a patient's treatment needs. In some cases, a properly trained patient can configure an infusion pump according to their individual requirements within pre-defined limits without the involvement of a physician. The physician or patient can program or configure the infusion pump by physical manipulation of a user interface according to certain physiological, pharmacokinetic, and operational parameters or limits that are often predefined.

In operation of an infusion pump, caution must be exercised to avoid certain error conditions that could be potentially harmful to a patient who is connected to the pump. For example, an air-in-line condition may cause serious harm to a patient if not addressed and corrected promptly. Typically, an air-in-line sensor triggers an alarm that stops the pump until a practitioner takes necessary action to remove the potentially harmful air from the infusate tubing or line. In some instances, a pump will have hardware and software that cooperate to automatically stop the pump upon detection of air in the line.

As described in a working draft of revisions to IEC 60601-2-24, which is quoted in part below, there has been discussion regarding the topic of stopping the pump upon occurrence of an alarm:

"Consider the scenario of infusing a potentially hazardous amount of air. An IV bag may run empty, and if the infusion pump keeps running, it could deliver air to the patient, resulting in an air embolism. To mitigate this risk, many infusion pumps implement an air detecting sensor, and will alarm and stop the pump if air is detected.

Proper risk management techniques tell us that the air sensor itself has failure modes. For example, the electrical signal voltage of the air sensor could become saturated, indicating a failure of the sensor such that the sensor might not detect if air is present. A traditional approach to this potential failure mode is for the device to perform periodic self-checks of the sensor to ensure it is operating correctly. If the sensor is found to not be operating correctly, a traditional approach would be to stop the infusion and notify the healthcare provider that the sensor has failed. When certain faults occur, stopping the infusion may be the safest option.

However, there many instances where the interruption of therapy introduced by the self-diagnostic system is actually a greater risk than a sensor that is unable to detect air. In the case of a failed air-sensor, air may or may not be present, therefore there may or may not be a hazardous situation present, however, when the infusion pump reacts by stopping the infusion, creating the hazardous situation interruption of therapy . . . . There are therefore instances where the safest thing for the infusion pump to do in the case of a detected failure is to continue infusing.

. . .

Fail operative design decisions will be made and implemented by the individual manufacturer; however the following considerations and examples are intended to aid the manufacturer in identifying common failure states and categories for infusion pumps and controllers.

For infusion pumps, determining the 'safest' way to fail can best be known in the context of the state of the pump, the drug being infused, patient condition, environmental conditions, etc. Historically, the infusion pump did not have these contextual elements, and the design decisions had to assume that safest option for most conditions is to fail-stop and alarm.

Although the pump will not necessarily know all relevant contextual factors, such as the patient condition, some pumps do have sufficient information to make more educated determinations regarding the risk/benefit of interruption an infusion vs. continuing to operate in a fail-operative mode. One example would be an infusion being delivered at a low infusion rate when a failure of the air sensor is detected; given the low infusion rate, even if there were an air bubble passing through the pump, it may take several hours for the air bubble to travel from the pump to the patient, and therefore an immediate stoppage of the infusion is not warranted. Another example would be a DERS library that has a configurable field that indicates which fluids are life-sustaining such that fail-operative mode is appropriate.

Regardless of the fault-tolerant strategy implemented for the ME equipment [("infusion pumps and volumetric infusion controllers")], accompanying documents should clearly describe each fault condition visible to the user and the ME equipment's behavior during those conditions."

While various syringe and LVP infusion pumps have been used in medical environments for many years, these devices remain rather complex medical devices with some limitations to their efficient, effective, and safe use. Therefore, there is a need for syringe pumps and LVPs which provide greater flexibility and ease of use to operators. Moreover, due to the vital role of infusion pumps in many medical procedures and treatments, syringe pumps and LVPs which provide enhanced safety to patients are needed as well.

SUMMARY

The subject matter hereof relates generally to medical devices, and more particularly, to systems and methods for improving operation of infusion pumps as described by example or otherwise contemplated herein.

In an example, an infusion pump can include a sensor, a pumping mechanism to deliver medicament through an infusion set to the user, and a processor operably coupled to the sensor and the pumping mechanism. The processor can be configured to receive an indication from the sensor of an error condition, and continue operating the pumping mechanism to deliver a predetermined quantity of medicament without correcting the error condition. The predetermined quantity can be based at least in part on a characteristic of the infusion set.

In an example, the present disclosure provides a system for improving operation of an infusion pump. The system can include an infusion pump; at least one sensor to detect an error condition such as undesirable air or an occlusion in tubing connected to the pump, or a sensor failure, in which said sensor generates and transmits at least one signal that is indicative of detection of the error condition; means for determining a downstream volume capacity of the tubing connected to the pump; software configured to be operative in response to receiving the at least one signal and in response to the means for determining a downstream volume capacity of the tubing such that when a safety factor is applied by the software to the downstream volume capacity, then an escalation metric of accumulated volume is defined that triggers a safe delay; means to warn or alarm that the safe delay has been triggered; and means to clear a safe delay warning or alarm. In some cases, the system can include means for determining a downstream volume capacity of the tubing connected to the pump, including means to determine a known volume capacity of the tubing between the sensor and an infusion site proximate a patient. As used herein, the term error condition may refer to any abnormal, undesirable, or otherwise adverse condition relating to pump operation, including system faults such as sensor or other hardware failures, and so-called "alarm conditions" which are typically associated with activation of an alarm and suspension of infusion such as air detected, occlusion detected, or similar.

In another illustrative but non-limiting example, the subject matter provides a method for improving operation of an infusion pump. The method can include detecting an error condition of an infusion pump, wherein said error condition includes air in a length of tubing leading to an infusion site in a patient, an occlusion in the tubing to the infusion site, or a failure of the sensor; generating and transmitting a warning or alarm that indicates the detection of the error condition; determining a downstream volume capacity of the tubing connected to the pump; and configuring software to apply a safety factor to allow continued operation of the pump before the error condition reaches a critical stage.

The above summary is not intended to describe each and every example or every implementation of the subject matter. The description that follows more particularly exemplifies various illustrative embodiments.

BRIEF DESCRIPTION OF THE DRAWINGS

The following description should be read with reference to the drawings. The drawings, which are not necessarily to scale, depict examples and are not intended to limit the scope of the disclosure. The disclosure may be more completely understood in consideration of the following description with respect to various examples in connection with the accompanying drawings, in which:

FIG. 2 is a flow diagram according to an embodiment of the disclosure.

Figure 1:
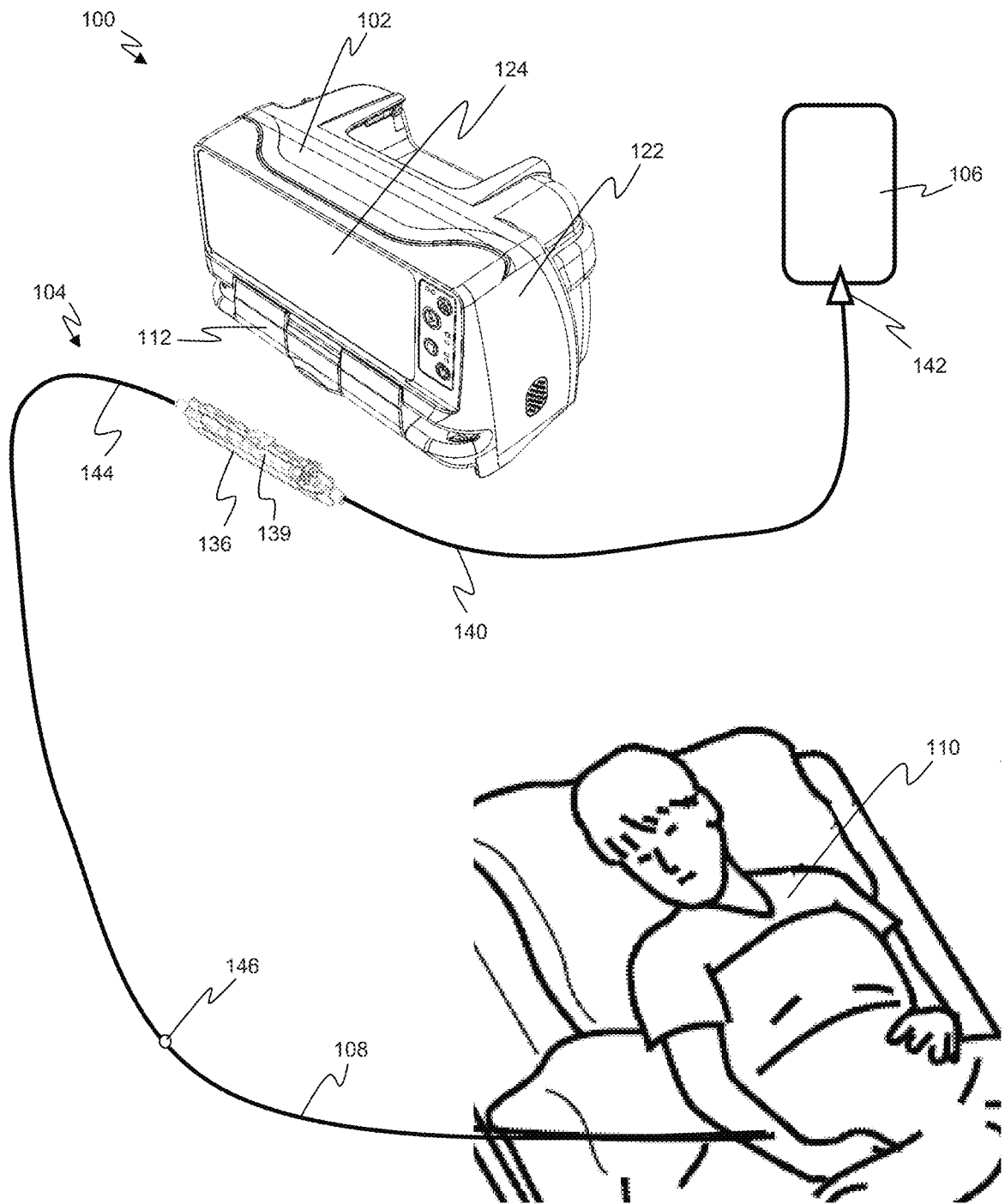
FIG. 1 is a schematic view of an infusion pump system that includes a LVP and administration set, according to an embodiment of the disclosure.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION OF THE DRAWINGS

The following description should be read with reference to the drawings, in which like elements in different drawings may be numbered in like fashion. The drawings, which are not necessarily to scale, depict selected examples and are not intended to limit the scope of the disclosure. Although examples of construction, dimensions, and materials may be illustrated for the various elements, those skilled in the art will recognize that many of the examples provided have suitable alternatives that may be utilized.

Embodiments of the present disclosure may be applicable to various types of infusion pumps. FIG. 1 depicts a schematic perspective view of an example embodiment of an infusion pump system 100 that includes a large volume (LVP) peristaltic pump 102 and a disposable administration set 104 that is structured and configured to operatively and removably couple to pump 102. Administration set 104 is shown providing a fluidic pathway from an IV bag 106 to an infusion set 108 that ultimately delivers infusate(s) to a patient 110. In FIG. 1, the receptacle door 112 of the peristaltic pump 102 is shown in a closed configuration and administration set 104 is illustrated as not coupled to pump 102.

Pump 102 includes a housing 122 and a user interface 124 (that can include, for example, a display screen, keypad, audio speaker, and any other suitable user interface components) for prompting and/or relaying commands to a control system or controller of pump 102, and/or for communicating from/to the controller to/from users. User interface 124 generally can allow a user to enter various parameters, including but not limited to names, drug information, limits, delivery shapes, information relating to hospital facilities, as well as various user-specific parameters (e.g., patient age and/or weight) along with so-called "five rights" verification or inputs. Pump 102 can include any appropriate wired or wireless input/output (I/O) interface port and/or protocol (including, but not limited to, USB, Ethernet, WiFi, NFC, Bluetooth, ZigBee, IrDA, and the like) for connecting pump 102 to a network or computer (not illustrated) having software designed to interface with pump 102.

User inputs to pump 102 can be provided by programming from an authorized user, such as a patient, pharmacist, scientist, drug program designer, medical engineer, nurse, physician, or other authorized medical practitioner or healthcare provider. User inputs may utilize direct interfacing (via, e.g., keyboards, touch screens, or other touch-based inputs) as shown, and/or user inputs may utilize indirect or "touchless" interfacing (i.e., gestures; voice commands; facial movements or expressions; finger, hand, head, body and arm movements; or other inputs that do not require physical contact such as cameras, sensors of electric field, capacitance, or sound). User inputs generally can be interfaced, communicated, sensed, and/or received by operator input mechanisms of user interface 124.

Administration set 104 can provide a fluidic pathway from an IV bag 106 or other infusate reservoir to an infusion set 108 that ultimately delivers infusate(s) to a patient 110. It is to be appreciated and understood that, although the present disclosure refers to an IV bag 106 or other infusate reservoir and an administration set 104, subject matter hereof could include or be applicable to a plurality of same, similar, or different infusate reservoirs, infusates, and administration sets. Administration set 104 can include or be coupled with, in addition to assembly 136, upstream tubing 140 that can extend from IV bag 106 or other reservoir to assembly 136. Upstream tubing 140 can terminate in a bag spike 142 or other connector. Administration set 104 can also include or be coupled with downstream tubing 144 that can extend from assembly 136 to infusion set 108. Downstream tubing 144 can be fluidically coupled to infusion set 108 or other catheter with connector 146 such as a Luer-type connector or any other suitable connector, such as one of those contemplated, specified, defined, or described by one of the ISO 80369 series of small bore connector standards. The administration set 104, infusion set 108, and various portions of tubing may be individually or collectively referred to as tubes, tubing, line, lines, disposables, disposable sets, or other terms as understood by persons skilled in the art.

Figure 1A:
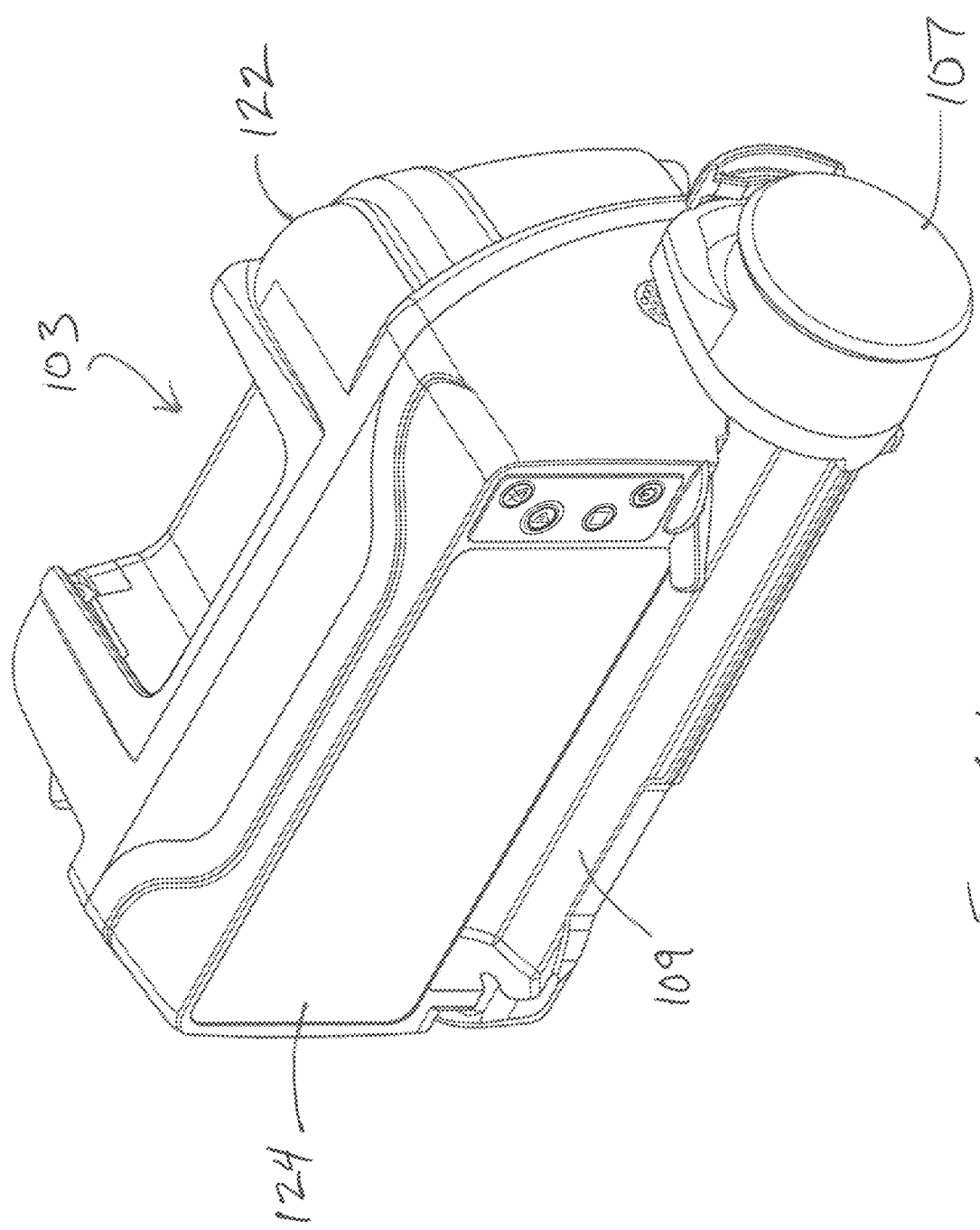
FIG. 1A is a perspective view of a syringe pump, according to another embodiment of the disclosure.

In another embodiment depicted in FIG. 1A, an infusion pump may comprise a syringe pump 103 including a housing 122, user interface 124, syringe drive assembly 107, and syringe receptacle 109. A syringe (not illustrated) is coupled to pump 103, and an infusion set or other tubing arrangement is connected to the syringe to provide a fluidic pathway to delivers infusate(s) to a patient. The syringe drive assembly 107 may include a force sensor configured to sense a force magnitude acting upon a syringe loaded into the syringe pump. In an embodiment, the force sensor can sense a force applied by the plunger driver assembly upon a syringe during operation. In an embodiment, the force sensor can be utilized to detect the presence of an occlusion.

An embodiment of the system for improving the operation of an infusion pump to detect air-in-line and yet continue operating in a "safe delay" mode without adversely affecting a patient receiving an infusate from the pump, includes: an infusion pump comprising at least one sensor adapted to detect undesirable air in the tubing connected to the pump and further adapted to generate and transmit at least one warning or air-in-line detection ("AILD") signal, i.e., air signal, that indicates the presence of an air bubble or other potentially harmful volume of air or unintended gas (collectively, "air") in the tubing; means to determine the downstream volume capacity of an infusate between the sensed air and an infusion site on a patient; means to calculate the rate of infusion: and software configured to be operative in response to receiving the at least one AILD signal and in response to the means for determining a downstream volume capacity of the tubing such that when a safety factor is applied by the software to the downstream volume capacity, then an escalation metric of accumulated volume is defined, which then triggers the safe delay mode.

By way of non-limiting example only, if a pre-determined volume of infusate in the tubing between the sensor and the infusion site is 10 ml, and the programmed infusion rate is 1 ml per minute, then upon the sensor detecting an air bubble and providing a warning signal, the pump may continue to operate and deliver infusate to the patient for up to about 10 minutes before the air reaches the infusion site and the pump is programmed to stop. In an embodiment, an infusion pump can also include a microprocessor further comprising a counter to automatically keep track of the time. An embodiment of a safe-delay infusion pump can include a programmed safety factor such as, for example, to stop the infusion after pumping 6 ml of infusate with an intermediate alarm upon pumping 3 ml of infusate.

In an embodiment, administration set 104 may take the form of a tubing frame assembly ("TFA") that would serve to standardize the volume of the infusate within the tubing and allow for relatively easy and predictable programming of the infusion pump. A suitable TFA is disclosed in International Patent Application (PCT) Pub. No. WO 2017/218927 A1, which is fully incorporated herein by reference. A further embodiment can include an algorithm that accounts for the length of tubing and the working parameters of the pump to calculate the period of delay before stopping the pump.

Another embodiment includes a cam flag, in which the safe delay period may be measured by the number of rotations of a cam in an infusion pump. When the cam rotations reach a certain limit, then the pump would be configured to issue a flag or warning to the caregiver.

By way of further non-limiting example, the safe delay trigger comprises coded disposables including color or RFID. For a large-volume pump, the TFA may include a color sensor or RFID system to determine the disposable set "limits" for safe delay. An optically-readable color sensor or RFID system can, for example, indicate the type and rate of infusate, or downstream volume (priming volume), or typical downstream pressure associated with the TFA.

To prevent or minimize accumulated AILD alarms or warnings from becoming a nuisance or confusing to a caregiver, an embodiment includes software adapted to clear accumulated AILD alarms or warnings or other counters that have been logging pump parameter information.

The aforementioned alarm or warning signal may include an escalating, multi-step alarm, such as an initial, medium-priority alarm, which could then escalate to a higher-priority alarm as the air moves closer to the infusion site of the patient. An embodiment can include an alarm-escalation feature similar to a low-battery alarm because healthcare providers often are already familiar with low-battery alarms on infusion pumps. In another embodiment, the alarm can be programmed, for example, to allow for a 2-minute delay before a final alarm is sounded or the pump automatically shuts off. By way of non-limiting example only, escalation of the alarm can include a color-coded alarm like yellow, orange, and red to indicate increasing priority, an increasingly louder audible tone, or an increasingly louder voice warning. Those of skill in the art will appreciate that an escalating warning system could include a combination of color, tone, and voice warnings.

Those of skill in the art will appreciate that the aforementioned embodiments, which are directed to AILD, are equally applicable to safely delay an infusion pump upon detection of upstream or downstream occlusions ("USO or DSO"). Similar to the example of a delay in stopping the pump upon an AILD alarm or warning, a sensor that detects an occlusion in or of the tubing can trigger a warning or alarm, yet can delay an immediate shut-down of the infusion pump or delay stopping the pump's infusion operation. Perhaps more typically for USO and/or DSO, detection by an infusion system or pump of a failure of a USO and/or DSO sensor itself can trigger a warning or alarm, but delay an immediate shut-down of the infusion pump or otherwise delay stopping the pump's infusion operation. In an embodiment, the system can be adapted to override the safe delay stop or suspend feature to allow sufficient time to investigate the occlusion to prevent or reduce the potential of a post-occlusion delivery of an unintended bolus of infusate, i.e., post-occlusion bolus reduction ("POBR").

Another non-limiting example of a system and method for improving the operation of an infusion pump includes means for detecting a sensor failure. In such an embodiment, the infusion pump would be programmed to trigger an alarm and delay shutting off by a pre-determined safety factor in a manner similar to detecting air-in-line. For example, the pumps' software may be configured to be operative in response to detecting the occurrence of a failure of a sensor, by determining a downstream volume capacity of the tubing such that when a safety factor is applied by the software to that downstream volume capacity, then an escalation metric of accumulated volume is defined that then triggers the safe delay. Those of skill in the art will appreciate that upon detecting a force sensor failure on a syringe, for example, a safe delay period will depend on the size (i.e., volume) of the syringe because the delta volume will be different for different syringe sizes. In another embodiment, the USO and the DSO sensors both show a relaxation characteristic. Accordingly, such a characteristic can be compared between the sensors. In an event of a mismatch or operational error, pump software could approximate the performance of one sensor based upon the performance of the other sensor. When used in coordination with known characteristics of an associated set of disposable infusate tubing, this could result in a pump system that would advantageously continue operating safely using the same escalation metric of accumulated volume for triggering a safe delay mode.

An embodiment of a system and method for improving the operation of an infusion pump can include a background self-test ("BST"), which can be adapted to monitor a desired number of system parameters. By way of non-limiting example only, if a BST determines that the AILD sensor has failed, it may nevertheless implement a delay and continue operation regardless of whether safe delay is enabled or not.

Other hardware failures could be handled separately from safe delay programming or a safe delay enabled mode of operation. For example, a separate protocol could be employed for other hardware failures, like hardware failures of syringe pumps such as, for example, Medfusion™, Intellifuse™, or CADD™ brand pumps and infusion systems, and failures of pump features such as, for example, Flow Sentry™ infusion anomaly detection systems. Such separate protocols can include immediate stoppage of the infusion pump whether safe delay is enabled or not.

A further embodiment of the infusion pump includes a network connected or connectable pump adapted to manually or automatically upload that pump's settings to a network server so that if the pump is replaced, the parameters of the replaced pump can be easily downloaded and substantially replicated or "cloned" to a replacement pump—including, for example, cloning parameters and features of a particular safe delay embodiment. The aforementioned "cloned" embodiment could also be implemented if BST determines a hardware failure, including but not limited to a sensor failure, so that when the pump is replaced, the settings can be downloaded from the server. In such a networked infusion pump system, an embodiment of the pump provides for limiting the pump parameters using a PharmGuard™ system ("PGS") or PharmGuard Creator ("PGC"), which allows a pharmacist to determine whether safe delay is enabled for a particular infusate profile. For example, a pharmacist may disable AILD for a routine nutritional or enteral feeding infusion profile. In contrast, a pharmacist may mandate AILD for a critical care infusion profile. An embodiment can also include PGS or PGC pump parameters that include upper and lower hard and soft limits that provide for absolute or flexible pump operational parameters. The foregoing example may, but not necessarily, be referred to as "SafeDelay per Care Area."

Embodiments of systems and methods for improving the operation of infusion pumps may further include means to allow the pump to continue operating should a sensor register a false positive. For example, if the infusate volume between the pump and the infusion site is 8 ml, then the pump could be configured to apply a safety factor so as to only deliver 6 ml of infusate (as calculated by a known rate of infusion) before shutting down the infusion pump or otherwise stopping the pump's infusion operation. Such an embodiment can include an alarm escalation point that is triggered at a particular volume of infusate delivered by the pump, e.g., half the stop limit, or 3 ml in this example.

As shown in FIG. 2, which is a non-limiting generalization of the system and method disclosed herein, the system and method includes an electronically-programmable infusion pump comprising at least one sensor 10. The sensor 10 is adapted to detect certain undesirable error conditions, including air in the tubing of the pump, an occlusion in the tubing of the pump, or a failure of the sensor itself 20. Upon detecting such an error condition, the pump is adapted to issue a warning or alarm to alert a caregiver that an error condition has occurred and activate a safe delay feature 30, which is adapted to keep the pump in operation mode depending on pharmacological or other factors for a certain period of time instead of shutting off or otherwise stopping its infusion operation immediately. The pump may further be adapted to escalate the warning or alarm 40, or not 50, as the safe delay period continues before the infusion pump shuts off or otherwise stops its infusion operation 60.

Figure 2A:
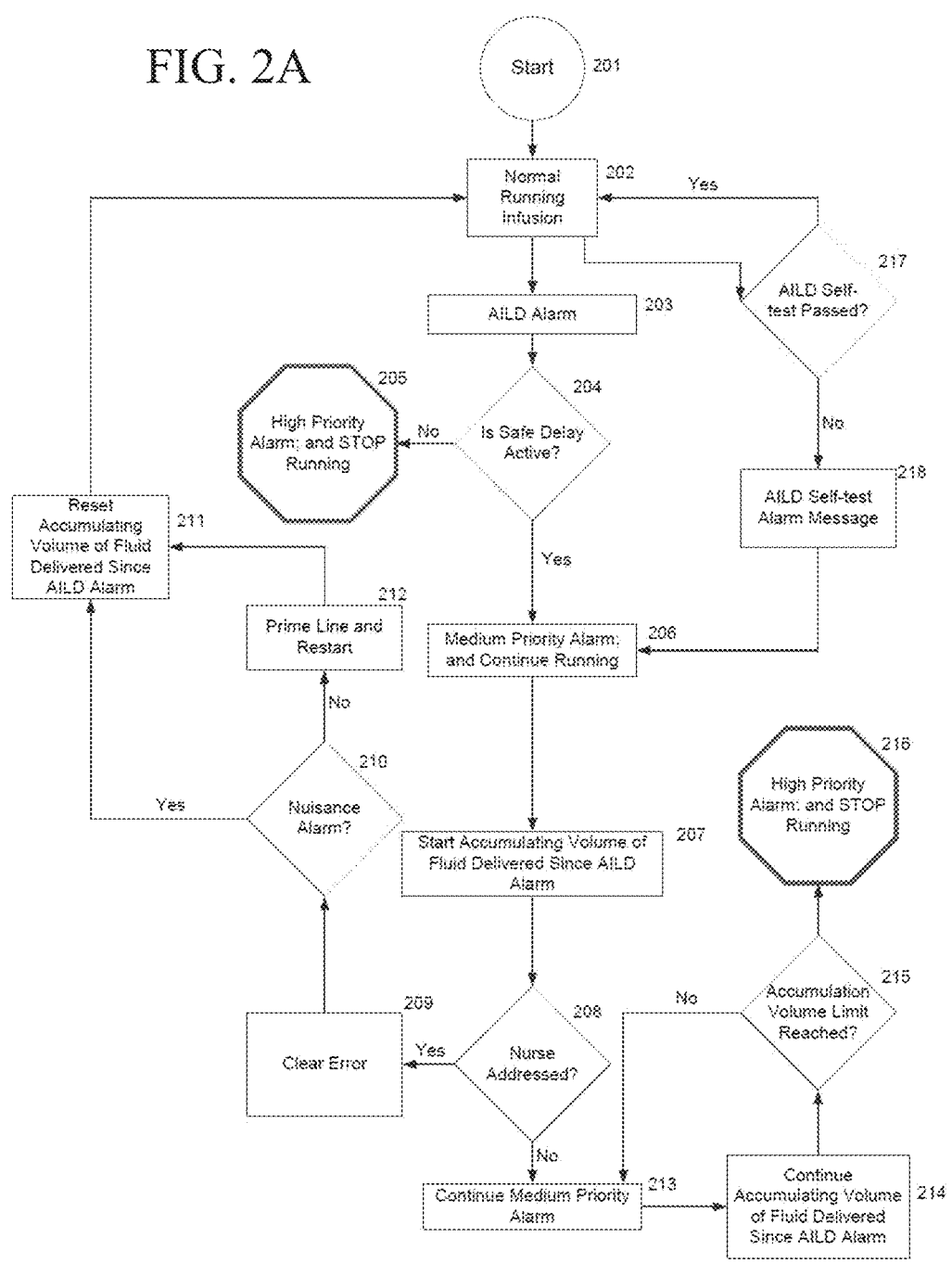
FIG. 2A is a flow diagram according to another embodiment of the disclosure.

As shown in FIG. 2A, which is another non-limiting generalization of the system and method disclosed herein, the system and method includes starting 201 the infusion 202 pump system, which is programmed to provide an infusate to a patient at a prescribed duration and rate. If the system detects an air bubble (AILD) in the infusate tubing, however, the pump is adapted to issue a warning or alarm to alert a caregiver to the AILD 203. If safe delay 204 has not been activated, then the pump can be programmed to issue a high priority alarm and cease operation immediately 205. If safe delay has been activated, however, the pump can be programmed to issue a low or medium warning or alarm— which can be determined by the type of infusate and the rate of infusion—and continue operation 206. Such continued operation could accumulate or record the volume and rate of the infusate delivered to the patient since the AILD alarm 207. This volume/rate or time calculation can be used to adjust the alarm priority, e.g., from a low to medium to high or urgent priority for example, based on a predetermined infusate volume limit.

If a nurse or other caregiver addresses the alarm 208, the caregiver can clear any erroneous alarm 209, determine if the alarm has merely detected a nuisance 210, such as when, for example, a patient receiving the infusion has rolled over onto a portion of the tubing and inadvertently occluded it, and then reset the pump and take into account the volume of infusate delivered to the patient since the AILD alarm 211. Alternatively, if a nurse or other caregiver addresses the alarm and determines it is other than a nuisance or inconsequential alarm, the caregiver can clear the occlusion or air that is present, prime the tubing, and restart the pump 212 and also take into account the volume of infusate delivered to the patient since the AILD alarm 211.

If a nurse or other caregiver does not address the alarm, the pump can continue to issue a warning or alarm, like a medium priority alarm for example 213, and continue accumulating or recording the volume and rate of the infusate delivered to the patient since the AILD alarm 214. Once the accumulated volume has reached a predetermined limit 215, the system can be adapted to continue issuing a warning or alarm, like a medium priority alarm for example 213, and continue accumulating or recording the volume and rate of the infusate delivered to the patient since the AILD alarm 214. In this embodiment, the alarm priority can increase as the time/volume decrease. The accumulation volume can be calculated as a function of the downstream volume of a TFA less a safety factor. A TFA can be adapted to include a color sensor and/or RFID, for example, that can inform the system on the TFA downstream volume. It is thus to be appreciated and understood that, although not explicitly illustrated in the drawings, a TFA and an associated set of disposable infusate tubing with any related accessories can be linked to an applicable safety factor of a particular embodiment of a system and method for improving the operation of infusion pumps. Essentially, therefore, the pump system can recognize that a particular TFA/tubing set is being loaded, and from that data recognize the typical length of tubing—and thus an approximate volume of infusate—with regard to the safety factor.

A safety factor can include, for example, a consideration of a sensor's ability to detect air bubbles of diminishing sizes, with application of a suitable scaling factor, metric, or range accordingly. Thus, for a particular sensitivity in detecting air, a safety factor can account for a selected percentage of predicted, estimated, or typical downstream volume of the infusate. It is to be appreciated and understood that such a safety factor feature can also be adapted to be applicable to a selected percentage of predicted, estimated, or typical upstream volume of the infusate. Alternatively, once the accumulated volume has reached a predetermined limit 215, the system can be adapted to cease operation, e.g., stop pumping 216.

The system can also include a BST function, for example, a self-test of the AILD sensor 217. Those of skill in the art will appreciate that BST is applicable to any pump sensor or other hardware failure. In such embodiments, if the system passes the BST, the pump can continue normal operation 202 until such time the system issues another warning or alarm 203. If the system fails a BST, however, the system can issue a BST warning or alarm message 218 and continue operation under a medium priority alarm for example 206.

Although not explicitly illustrated in the drawings, it is to be appreciated and understood that data may be taken and/or logged upon selected occurrences of operation of a safe delay mode. Such data may include the frequency of occurrences, in what locations they are occurring, occurrences associated with particular pump systems and/or particular practitioners, alarm response times, and escalation occurrences. This data can then, for example, provide desired feedback or inputs to a system "learning" feature or to any suitable or desired administrative and/or patient care quality review process.

This disclosure is to be understood to be not limited to the particular examples described herein, but rather should be understood to cover all aspects of the disclosure and equivalents thereof. Various modifications, processes, and components, as well as numerous devices to which the disclosure can be applicable, will be readily apparent to those of skill in the art upon review of this disclosure.

The invention claimed is:

1. An infusion pump, comprising:
   a sensor;
   a pumping mechanism to deliver medicament through an infusion set to a user; and
   a processor operably coupled to the sensor and the pumping mechanism, the processor configured to:
   receive an indication from the sensor of an error condition;
   continue operating the pumping mechanism to deliver a predetermined quantity of the medicament without correcting the error condition, the predetermined quantity being based at least in part on a characteristic of the infusion set,
   wherein the processor is further configured to generate an alarm in response to the error condition, and
   wherein the processor is further configured to escalate the alarm prior to completion of delivering the predetermined amount of medicament.

2. The infusion pump of claim 1, wherein upon completion of delivering the predetermined quantity of the medicament, if the error condition has not been corrected, the processor is further configured to stop operating the pumping mechanism.

3. The infusion pump of claim 1, wherein the predetermined quantity of the medicament is further based on a rate of infusion.

4. The infusion pump of claim 1, wherein the characteristic of the infusion set comprises a volumetric capacity of the infusion set.

5. The infusion pump of claim 4, wherein the predetermined quantity of the medicament is less than or equal to the volumetric capacity of the infusion set.

6. The infusion pump of claim 1, wherein the error condition comprises detection of air.

7. The infusion pump of claim 1, wherein the error condition comprises detection of an occlusion.

8. The infusion pump of claim 1, wherein the error condition comprises failure of the sensor.

9. A method of operating an infusion pump, the infusion pump including a sensor, a pumping mechanism to deliver medicament, and a processor operably coupled to the sensor and the pumping mechanism, the method comprising:
  operating the pumping mechanism to deliver medicament through an infusion set to a user;
  receiving at the processor from the sensor an indication of an error condition;
  causing the pumping mechanism to deliver a predetermined quantity of medicament without correcting the error condition, the predetermined quantity being based at least in part on a characteristic of the infusion set,
  generating an alarm in response to the error condition, and
  escalating the alarm prior to completion of delivering the predetermined amount of medicament.

10. The method of claim 9, further comprising:
  stop operating the pumping mechanism upon completion of delivering the predetermined quantity of medicament if the error condition has not been corrected.

11. An infusion pump, comprising:
  a sensor;
  a pumping mechanism to deliver medicament through an infusion set to a user; and
  a processor operably coupled to the sensor and the pumping mechanism, the processor configured to:
    receive an indication from the sensor of an error condition;
    continue operating the pumping mechanism to deliver a predetermined quantity of the medicament without correcting the error condition, the predetermined quantity being based at least in part on a characteristic of the infusion set,
  wherein the error condition is detection of air, detection of an occlusion, or failure of the sensor.

* * * * *